United States Patent [19]

Hill

[11] 4,230,601

[45] Oct. 28, 1980

[54] CALIBRATOR COMPOSITION BASED UPON DIALYZED BLOOD SERUM

[75] Inventor: Doyle E. Hill, Fairport, N.Y.

[73] Assignee: Eastman Kodak Company, Rochester, N.Y.

[21] Appl. No.: 902,605

[22] Filed: May 3, 1978

[51] Int. Cl.³ .................. C09K 3/00; G01N 33/16; G01N 31/14; G01N 31/22

[52] U.S. Cl. .................. 252/408; 23/230 B; 422/68; 424/3; 424/7; 424/101; 435/4; 435/10; 435/11; 435/14; 435/25; 435/28

[58] Field of Search ............... 252/408; 23/230 B; 195/99, 103.5 R; 424/3, 7, 101; 435/4, 10, 11, 14, 25, 28; 422/68

[56] References Cited

U.S. PATENT DOCUMENTS

| | | | |
|---|---|---|---|
| 2,986,453 | 5/1961 | Collins | 252/408 |
| 3,063,812 | 11/1962 | Collins | 252/408 |
| 3,438,737 | 4/1969 | Atkinson et al. | 252/408 |
| 3,528,777 | 9/1970 | Moran | 252/408 |
| 3,533,749 | 10/1970 | Kleinman | 252/408 |
| 3,558,278 | 12/1971 | Louderback et al. | 252/408 |
| 3,751,381 | 8/1973 | Megraw | 252/408 |
| 3,754,865 | 8/1973 | Gindler | 252/408 |
| 3,802,842 | 4/1974 | Lange et al. | 252/408 |
| 3,922,145 | 11/1975 | Turner et al. | 252/408 |
| 3,955,925 | 5/1976 | Proksch et al. | 252/408 |
| 3,960,492 | 6/1976 | Diciulio | 252/408 |
| 3,992,158 | 11/1976 | Przybylowicz et al. | 23/230 B |
| 4,007,008 | 2/1977 | Decker et al. | 252/408 |
| 4,069,016 | 1/1978 | Wu | 23/230 B |

OTHER PUBLICATIONS

Kraugh-Hansen, U., et al., Biochem. Biophys. Acta., vol. 365, pp. 360-371 (1974).

Doumas, B., et al., Clin. Chim. Acta., vol. 31, pp. 87-96 (1971).

Miyaba, D., et al., Clin. Chem., vol. 18, No. 1, pp. 52-56 (1972).

*Primary Examiner*—Teddy S. Gron
*Attorney, Agent, or Firm*—Dana M. Schmidt

[57] ABSTRACT

A calibrator composition is disclosed in which a bias due to a dialyzed blood serum matrix is reduced to an acceptable level by the addition of a compatible, organic material. Methods of preparing and using the same are also disclosed.

9 Claims, 1 Drawing Figure

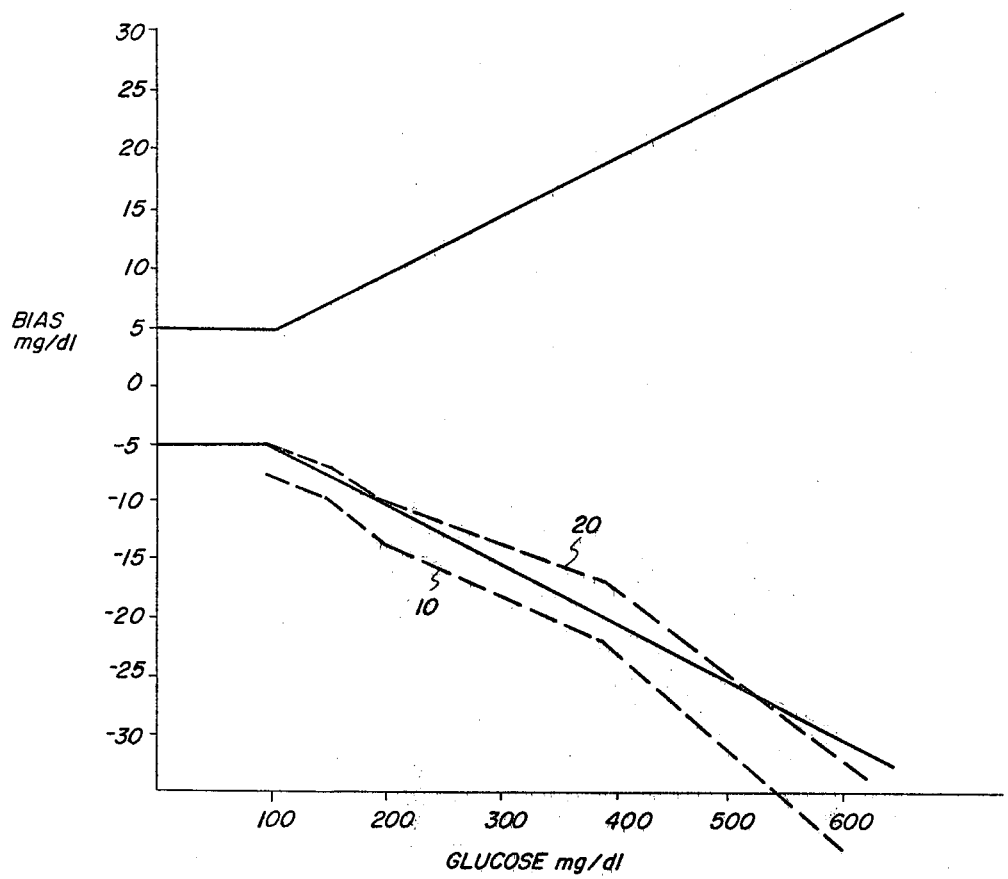

CALIBRATOR COMPOSITION BASED UPON DIALYZED BLOOD SERUM

FIELD OF THE INVENTION

This invention relates to a composition for the calibration of clinical analysis test elements useful in quantitating the levels of blood analytes. Methods of preparing and using the same are also disclosed.

BACKGROUND OF THE INVENTION

Automated clinical analyzers relying upon radio-metric detection of a change in absorption require calibration using a "standard" or calibrator. Such calibrators usually require two or more known concentrations of an analyte of choice, such as glucose, to be fixed at specific levels of the measured characteristic, e.g., reflection or transmission density. From these a "calibration" curve is derived for use with readings for unknown analyte concentrations.

It is conventional, in the preparation of calibrators, to separate the small molecular components and ions from the blood serum matrix and then to add back to the matrix the materials of choice to certain pre-selected levels for that particular calibrator. Such separation commonly is achieved by dialysis. "Dialysis" as used in this application includes not only non-pressurized equalibrating flow of such small molecular components through a semi-permeable membrane, filter or permeable gel away from the matrix, but also ultrafiltration and diafiltration which rely upon a pressure assist to force such small molecular components to flow through the filter away from the matrix. Dialysis separation has now been found to strip materials which complex or otherwise bind with various components of the matrix, for example, bilirubin which complexes with matrix protein, e.g., albumin. Such stripping leaves the protein of the matrix with vacant sites capable of complexing or binding a variety of other organic molecules. The binding capability of these sites was known, however, only with respect to certain specific materials.

It is these dialyzed serum based calibrators which have been found to create a problem when used with various kinds of analytical reagents, whether the reagents are in liquid form in a container or are disposed in dried form in a test element. The reagents are relied upon to create a radiometrically-detectable change, and accordingly must be readable by a radiometer at a known wavelength of detection. The presence in a calibrator of a protein with free binding sites can remove the reagent from the detection area, particularly when using the dried, test element form. The reagent can also shift its wavelength of absorption away from the expected wavelength by binding to the free sites. A wavelength shift is a problem no matter whether the reagents are in liquid form or dried prior to use.

Considering first the nondetection of the reagents, this occurs, for example, in certain dried test elements used for assaying analytes, wherein an opaque porous overlayer is applied to a reagent layer. The porosity of the opaque layer may be such that the protein of a serum-based calibrator, when applied thereto, is retained. When this happens, free sites on the retained protein, e.g., retained albumin, can attract and bind the indicator reagent if such reagent is migratable. The porous layer retaining the albumin in effect competes with the reagent layer for the reagent used for detection. Less reagent is available for detection in the reagent layer, and it cannot be detected in the opaque overlayer.

Examples of dry test elements susceptible to the phenomenon of applied albumin being retained in an opaque overlayer where it attracts indicator dye, are disclosed in U.S. Pat. No. 3,992,158 issued Nov. 16, 1976. This patent describes a multilayer analytical element comprising in one embodiment thereof an opaque spreading layer and a reagent layer, the element being capable of producing a dye density which is proportional to the concentration of the analyte of choice when the spreading layer is contacted with a drop of sample solution. Such an element can be used to detect quantitatively a wide variety of analytes, through the use of, for example, migratable dyes. Such dyes migrate between the spreading layer and the reagent layer in the presence of liquid. The problem is that when calibrators comprising a dialyzed serum matrix or albumin are used with these analytical elements, a consistent negative bias occurs. That is, the amount of dye which is detected is always less than the amount one would expect. Such negative bias in many cases falls outside acceptable ranges of accuracy. This effect occurs wherever a migratable dye is used, so that it is not limited necessarily to the assay for any one particular analyte, such as glucose.

Other analytical elements capable of producing the same negative bias when calibrated with a dialyzed serum matrix include, for example, those shown in U.S. Pat. No. 3,802,842, issued Apr. 9, 1974, and Belgian Patent No. 837,939, published on May 14, 1976.

As noted, a second undesirable aspect of the binding of dyes to the free sites of the protein is that such binding tends to cause a shift in absorption wavelengths. If the analysis is based upon the amount of absorbance occuring at the wavelength before the shift, any binding of the substance will reduce the amount of absorbance that is detected. Bilirubin is one example. Unbound bilirubin has its maximum absorbance at 435 nm, while bilirubin bound to ablumin has such absorbance at 460 nm.

Various organic materials such as bilirubin, phenol-sulfophthalein dyes, 1-anilino-8-naphthalene sulfonate, fatty acids and L-thyroxine which are known to bind to the active sites of an albumin molecule are discussed in Kragh-Hansen et al "Protein Binding of Small Molecules", *Biochimica et Biophysica* Acta. 365 (1974) p. 360.

RELATED APPLICATIONS

Commonly owned U.S. Application Ser. No. 759,530 filed on Jan. 14, 1977 by T. Wu, now U.S. Pat. No. 4,069,016, entitled "Assay for Bilirubin" discloses a bilirubin test composition wherein a detectable dye is released from albumin in proportion to the amount of bilirubin present in the serum under analysis.

SUMMARY OF THE INVENTION

In accord with the present invention there is advantageously featured a calibrator composition, and a method of preparing the same, which comprises a dialyzed serum matrix and does not exhibit unacceptable biases in the calibration process.

In accord with a further aspect of the invention, there is also advantageously featured a reduced-bias calibration method using such a calibrator composition.

Said features of the invention are achieved by an improved calibrator composition for use in calibrating an analytical system in which an aqueous albumin-containing liquid is assayed for one or more non-proteinaceous analytes contained therein. These calibrator compositions comprise, in admixture, a pre-selected amount of such analytes, a blood serum matrix comprising albumin having free binding sites, and in particular a compatible, organic albumin site-binding material to bind to the free binding sites, thereby reducing the bias arising from the presence of free binding sites.

Such a composition is prepared by the steps of dialyzing a blood serum matrix to separate albumin from molecules at least as small as those having a molecular weight of about 1,000, and adding to the albumin, in either order, a pre-selected amount of a non-proteinaceous analyte and a compatible organic, albumin site-binding material, thereby reducing the bias arising from the presence of free binding sites.

Calibration preferably is achieved, pursuant to the invention, by the steps of (a) adding to successive test compositions at least two samples of a calibrator composition each of which comprises at least a different pre-selected amount of the analyte, a blood serum matrix including albumin having free binding sites, and a compatible, organic albumin site-binding material capable of binding to said free sites; (b) measuring the density of dye in the test composition; and (c) thereafter attributing the density measured to the pre-selected analyte amounts, whereby a calibration curve can be established for density measurements of samples other than those detected in the calibration step.

As used herein, "compatible albumin site-binding material" or "compatible organic material" means material which does not itself interfere with the analysis of choice. Thus, compatible materials are those having no significant absorbance at the wavelength chosen to examine the test element, and no other interfering property.

Also as used herein, "reduction in bias" and "to reduce the bias" means an amount and by an amount, respectively, which is more than experimental error, that is, an amount that is a significant decrease or increase. The terms "significant decrease" and "significant increase" are used in the statistical sense to mean a decrease and increase, respectively, beyond that which is explainable as a Student's t statistic for the number of tests actually run.

BRIEF DESCRIPTION OF THE DRAWINGS

The FIGURE is a plot of bias in mg/dl against actual amount of glucose detected, by using a calibrator composition prepared in accordance with the invention, compared to a control.

DESCRIPTION OF THE PREFERRED EMBODIMENTS

The composition of the invention is based upon the discovery that the objectionable bias discussed above was created by the binding of the particular migratable indicator dyes produced by the test element in response to the analyte, to proteinaceous materials in the calibrator, e.g., albumin, having free sites. The binding of the dyes to proteins such as albumin created because in the preferred use, the proteins are retained in an aqueous spreading layer where dye cannot be detected.

It will be readily appreciated that the largest representative of the serum proteins, at least in terms of mole percent, is albumin. For this reason, the discussion hereinafter is directed to the binding of free sites of albumin by means of the invention. However, it is possible that other proteins also may be affected similarly.

In most instances, the undesirable bias appears as a negative bias, i.e., less dye is detected than should be. The reason is that most applications rely upon the generation of dye as an indication of the amount of analyte present. The preferred embodiments hereinafter discussed involve the reduction of negative bias. However, the invention is also applicable to subtractive dye systems, wherein dye is destroyed as a measure of analyte, and in such instances the bias which is overcome by the invention is a positive one.

The composition of the invention can be used as a calibrator of any analyte, the test for which relies upon the density measurement of a dye, either preformed or formed in situ. The calibrator composition of the invention is particularly useful in calibrating the assay for glucose, cholesterol, triglycerides and uric acid. A wide range of amount of analyte can be so calibrated. For example, the calibration can contain from about 50 to about 800 mg/dl of glucose.

It has been found that many dyes used for the detection of analytes will strongly adhere to dialyzed albumin at the free dye-binding sites that are made available in the dialysis process, as described above. Such indicator dyes can be found in a variety of test substrates, and the calibrator composition of the invention can be used with any such substrates. Both dried test elements and liquid substrates can be calibrated by this invention. Examples include multilayer analytical elements such as those disclosed in U.S. Pat. Nos. 3,992,158 and 3,802,842. The calibrator composition of the invention is particularly useful for test elements which use a migratable indicator dye, i.e., one that is not mordanted, and an opaque overlayer used to obtain a uniform concentration of sample prior to contact with indicator reagents. As heretofore noted, such test elements tend to confine the albumin of the calibrator to the opaque layer. The migration of the indicator dye to the albumin in the opaque layer creates an undesirable negative bias as described in the "Background", except when the calibrator composition of the invention is utilized.

The calibrator compositions of the invention can be used to calibrate analyzers, and also can be used as controls to obtain more approximate machine adjustments, as is well known.

Examples of indicator dyes useful for testing an analyte, including any one of the four analytes noted above, and with which the calibrators of the invention can be used, include those in the following Table 1. The amount of each indicator dye will of course vary, depending upon the analyte for which it is used and the range of concentrations intended. The selection of actual amounts within these guidelines is conventional.

TABLE 1—DYES

I. Tetra-substituted phenylenediamines, e.g. those having the formula

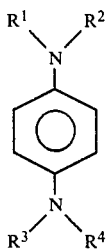

wherein $R^1$, $R^2$ and $R^3$ are the same or different and are each alkyl containing from 1 to 5 carbon atoms, and $R^4$ is alkyl or alkoxy containing from 1 to 5 carbon atoms;

II. Cyanine dyes, e.g. those having the formula

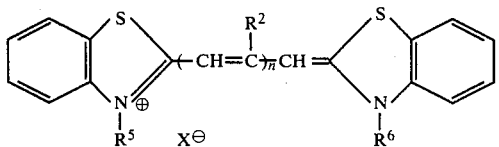

wherein $R^5$ and $R^6$ are hydrogen or are as $R^1$ defined above, n is an integer of from 0 to 7, and $X^\ominus$ is a suitable anion;

III. Dyes resulting from oxidative coupling of substituted naphthols, e.g. 7-hydroxy-1-naphthol, phenols, pyrazolones and other compounds containing an active methylene moiety, with 4-aminoantipyrene; and IV. Dyes resulting from the self-coupling of compounds such as 4-isopropoxy-1-naphthol and 4-methoxy-1-naphthol.

The added, compatible organic material, also referred to herein as bias-reduction material, which is selected will depend in part on a number of factors which can vary. In part it will depend on the dye that is being used in the indicator layer, and on the competitive binding level or attraction that that dye has for dialyzed albumin. Preferably, the bias-reduction material is selected to be one which has a greater affinity for the albumin than does the reagent dye. However, a material which has a weaker affinity can also be used, if used in greater concentration, as such concentrated material also will reduce the bias significantly. Comparative abilities of various materials to bind to albumin are disclosed in the literature, for example, the aforesaid Biochimica article, and reference can be made to such comparative abilities in the selection of the material.

Also, the material selected will depend in part on whether long-term stability is desired, as when long storage is likely. In such a case, the material used is one known to have such stability, for example, uric acid.

Useful examples for bias-reduction material capable of occupying the dye-binding sites of components of the dialyzed serum matrix include also various organic dyes having absorption wavelengths which are sufficiently removed from the wavelength at which the analyte is measured as to have essentially no absorbance at the latter wavelength.

As will be apparent, the bias-reduction material that is selected preferably is one that is not the analyte for which the calibrator is being prepared, unless the amount of analyte that is added is increased to account for the portion which is to bind to the free sites, and therefore which is to become undetectable. For example, a bilirubin calibrator using bilirubin as the bias-reduction material must take into account that some of the bilirubin will bind to the dialyzed albumin instead of being available as the analyte.

Particularly useful examples of such bias-reduction material that is added to the calibrator composition in accordance with the invention are listed in Table 2.

Table 2 alkyl sulfate and sulfonates such as dodecylsulfate and dodecylsulfonate
phenolsulfophthalein dyes such as bromphenol blue
salicylates such as sodium salicylate and acetyl salicylate
merthiolate
bilirubin
aromatic sulfonates such as 1-anilino-8-naphthalene sulfonic acid and aminonaphthalene sulfonic acid
L-thyroxine
palmitate
uric acid
N-benzyl derivatives of 3-chloro-6-methoxy-9-aminoacridine
vasoflavine
2-(4'-hydroxybenzeneazo) benzoic acid To determine whether or not a particular biasreduction material is useful at a particular concentration, the candidate can be incorporated into a complete calibrator composition prepared as described hereinafter, and tested on a complete test element. Or alternatively, the following simplified test procedure can be used.

A simplified test element is prepared by coating a registration layer onto a suitable support, in the manner taught in U.S. Pat. No. 4,042,335 to P. Clement on Aug. 16, 1977, the details of which are expressly incorporated herein by reference. For this test such a layer is to be free, as manufactured, of indicator dyes, but is permeable to such dyes as come into fluid contact with it. As noted in Clement, the layer can comprise a hydrophilic colloid such as gelatin, and preferably a mordant to retain a dye in the layer.

An overcoat comprising a spreading layer is prepared and coated over the registration layer in a manner taught by the aforesaid Clement patent, except that the layer also includes one of the dyes shown in Table 1.

After the simplified test element is dried, now comprising a registration layer and an overcoat layer containing, for example, 0.779 mg/dm² of 5-[(7-hydroxy-4-oxo-1(4H)-naphthylidene)amino]-2,3-dimethyl-1-phenyl-3-pyrazolin-5-one, two aqueous test drops, 10 μl each, are prepared. Each drop contains in solution about 7 g/dl dialyzed albumin, and only one of the drops also contains the candidate bias-reduction material in the concentration to be tested. Half of the simplified test element prepared as described is spotted with one drop, and half with the other. The amount of dye which migrates through the spreading layer into the registration layer for each test drop is then detected photometrically with a reflectometer set to measure the appropriate wavelength, e.g., 540 nm when the indicator dye is 5-[(7-hydroxy-4-oxo-(4H)-naphthylidene) amino]-2,3-dimethyl-1-phenyl-3-pyrazolin-5-one. The two readings are compared. If the density due to the drop containing the candidate is significantly altered compared to the control drop, then the candidate at the concentration tested has demonstrated the ability to bind to albumin preferentially as compared to the dye, and thereby function as a bias-reduction material. If not, either increased concentration of the candidate should be tested, or another candidate tested.

As will be readily apparent, the amount of the reduction in bias that is achieved by the invention will depend both on the relative affinity of the bias-reduction material for albumin compared to the affinity of the indicator dye, and on the concentration of the material used. In one form of the invention, sufficient material capable of occupying the albumin sites is added to reduce the bias to a point where the absolute value of the bias is no more than about 5%, or for less than 100 mg/dl of analyte, to no more than about 5 mg/dl actual error, whichever is greater. Such bias levels have been selected by the FDA as a product class standard for the detection of glucose, 39 Fed. Reg. No. 126, June 28, 1974, p. 24136, and hereinafter will be referred to as "the Federal Standard". For example, glucose calibrators for test elements using 5-[7-hydroxy-4-oxo-1(4H)-naphthylidene)amino]-2,3-dimethyl-1-phenyl-3-pyrazolin-5-one as the indicator dye, and bilirubin as the added bias-reduction material, demonstrate a reduction in negative bias to within 5%, the Federal Standard, with a little as about 1 mg/dl of bilirubin. However, if 8-anilino-1-naphthalene sulfonic acid (ANS) is substituted for bilirubin in the above test, 10 mg/dl of ANS demonstrates a significant decrease in bias. More than 10 mg/dl was found to be required, e.g. about 50 mg/dl, to achieve a Federal Standard negative bias of only 5% across the full range of glucose values normally tested. Again, repeating the same test but using uric acid, it was found that about 6 mg/dl of uric acid reduces the bias to within the Federal Standard levels.

Other additives to the calibrator composition include pre-selected amounts of the analyte for which the composition is a calibrator, e.g., glucose, cholesterol, or the like. The composition can include still other analytes, particularly if a so-called "universal calibrator" is desired. The manner in which the analytes are prepared and incorporated is conventional, so that further discussion is unnecessary.

In accordance with another aspect of the invention, the calibrator composition is prepared first by dialyzing any suitable blood serum matrix, human or bovine, to separate albumin from small particulate and molecular matter, e.g. from at least those as small as 1000 in molecular weight (dalton units). Larger molecules can also be separated, up to those as large as about 20,000 molecular weight (MW). Such dialysis is done in a conventional manner, using one or more of the three separation processes noted above and a suitably sized membrane, e.g. one having a 1000 MW nominal cut-off, or a 20,000 MW nominal cut-off, etc. For example, "Spectropore" membranes manufactured by Fisher Scientific can be used. Such dialyzed serum, now predominantly albumin with free dye-binding sites, can then be further treated fresh, or it can be lyophilized and stored for later use.

Alternatively, a predialyzed serum matrix can be purchased and formulated into a calibration composition by the incorporation of the necessary additives.

When ready for use, the necessary additives, e.g. the site binding material and analyte, are incorporated either directly into the fresh dialyzed serum matrix, or by preparing an aqueous solution thereof to reconstitute the lyophilized form of the dialyzed matrix.

The calibrator composition prepared as described above is used to calibrate a test element in the conventional manner, i.e., simply by spotting successive elements with at least two different analyte levels of the composition. Then the dye density produced at those analyte levels is measured and these densities are thereafter attributed to these analyte levels or amounts. For two such analyte amounts, a straight line can be drawn to establish the calibration for points other than the two actually measured. Alternatively, additional levels of analyte can be calibrated and a curve fitted to these points, in a conventional manner.

EXAMPLES

The following representative examples further illustrate the nature of the invention.

For each of the following examples, a multilayer analytical test element for glucose was prepared as taught by the aforesaid U.S. Pat. 3,992,158, using as co-reactive indicator reagents, 4-aminoantipyrene (0.86 g/m$^2$) and 1,7-dihydroxynaphthalene (0.64 g/m$^2$).

Each of the bias-reduction materials was dissolved in water and the aqueous solution was used to reconstitute lyophilized, bovine serum dialyzed by using a "Spectropore" membrane manufactured by Fisher Scientific. Calibrators made from these solutions were compared to those made from lyophilized, dialyzed bovine serum which were reconstituted with water alone to form a control.

The aforementioned glucose analytical elements were then spotted with calibrator solutions comprised of the dialyzed, lyophilized bovine serum (control) and dialyzed lyophilized bovine serum containing one of the organic additives, as described. They are also spotted with a control calibrator prepared from a human serum pool to determine actual bias. Ten μl drops of each calibrator solution (7 levels of each) were spotted in random order onto the elements. At least six replicates were obtained at each concentration level.

The glucose concentrations were predicted from the solutions of bovine serum, with and without the bias-reduction additive, using a calibration curve derived from values obtained from the human serum pool using the hexokinase method as a reference. Bias, relative to the hexokinase reference assay, was computed.

The glucose reaction density for all tests was monitored on a reflectometer at 540 nm and at 37° C.

EXAMPLE 1

6 mg/dl uric acid was added as the bias-reduction material to solutions of lyophilized bovine serum containing from 100–600 mg/dl glucose. When spotted onto the test element as described above, this calibrator and the above-described bovine serum control generated bias curves. As shown in the FIGURE, curve 10 is the control, and curve 20 the composition containing uric acid. Although control curve 10 was outside the Federal Standard represented by the funnel shape, due to an unacceptable negative bias, the composition containing the uric acid was within the Federal Standard, as far as the experimental error (2%) for the number of tests that were run permits.

Similar results are available for a calibrator composition containing from about 50 to about 800 mg/dl of glucose.

EXAMPLE 2

Example 1 was repeated except that 10 mg/dl of ANS, magnesium salt, was used as the bias-reduction material. A significant decrease in negative bias was detected for the full range of glucose values.

EXAMPLE 3

Example 1 was repeated except that 1 mg/dl of bilirubin was used as the bias-reduction material. A significant decrease in negative bias was detected for the full range of glucose values. The calibrator composition containing the bias reduction material produced results that were within the Federal Standard.

The invention has been described in detail with particular reference to certain preferred embodiments thereof, but it will be understood that variations and modifications can be effected within the spirit and scope of the invention.

What is claimed is:

1. In a calibrator composition for use in calibrating an analytical system in which an aqueous albumin-containing liquid is assayed for one or more non-proteinaceous analytes contained therein by an indicator that binds to albumin having free sites, said composition comprising, in admixture
   a pre-selected amount of such analytes and
   a blood serum matrix comprising albumin having free-binding sites;
   the improvement wherein said composition contains a compatible, organic, albumin site-binding material in an amount sufficient to reduce the bias arising from the presence of said free-binding sites.

2. A composition as defined in claim 1, wherein said analyte is glucose, in an amount between about 50 and about 800 mg/dl.

3. In a reduced-bias calibrator composition for calibrating an analytical system for the assay of non-proteinaceous analytes by an indicator that binds to albumin having free sites, the composition comprising, in admixture,
   a pre-selected amount of analyte and
   a blood serum matrix comprising albumin separated from molecules at least as small as those having a molecular weight of about 1,000, said albumin having free dye-binding sites formed by said separation;
   the improvement wherein said composition contains a compatible, organic material capable of occupying said sites, in an amount sufficient to reduce the bias arising from the presence of free-binding sites.

4. A composition as defined in claim 3, wherein said analyte is glucose, in an amount between about 50 and about 800 mg/dl.

5. In a calibrator for calibrating an analytical system for the assay of a non-proteinaceous analyte by an indicator that binds to albumin having free sites, said calibrator comprising, as a composition,
   a pre-selected amount of the analyte and
   a dialyzed blood serum matrix comprising albumin having free-binding sites;
   the improvement wherein said calibrator contains a compatible, organic albumin site-binding material in an amount sufficient to reduce the bias arising from the presence of free-binding sites.

6. A method of preparing a reduced bias calibrator composition for calibrating an analytical system for the assay of non-proteinaceous analytes by an indicator that binds to albumin having free sites, comprising the steps of
   (a) dialyzing a blood serum matrix to separate albumin from molecules at least as small as those having a molecular weight of about 1,000; and
   (b) adding to said albumin, in either order, a pre-selected amount of a non-proteinaceous analyte and a compatible organic, albumin site-binding material in an amount sufficient to reduce the bias of the composition arising from the presence of free-binding sites.

7. A method of calibrating an analytical system for the assay of a predetermined analyte, using a substrate capable of generating a dye in response to the analyte, said dye being capable of binding with albumin having free sites, the method comprising the steps of
   (a) adding to successive test compositions at least two samples of a calibrator composition comprising at least two different pre-selected amounts of said analyte, a blood serum matrix including albumin having free-binding sites, and an amount of a compatible, organic albumin site-binding material sufficient to bind to said free-binding sites and to reduce the bias arising from the presence of free-binding sites;
   (b) measuring the density of said dye in the test composition; and
   (c) thereafter attributing the density measured to the pre-selected analyte amounts, wherein a calibration curve can be established for density measurements other than those detected in said measuring step.

8. A calibrator composition for use in calibrating an analytical system in which an aqueous liquid is assayed for one or more non-proteinaceous analytes contained therein by an indicator that binds to albumin having free sites, said composition comprising, in addition to said analytes,
   (a) a blood serum matrix comprising albumin having free-binding sites; and
   (b) a compatible, organic, albumin site-binding material in an amount sufficient to reduce the bias arising from the presence of said free-binding sites.

9. A composition as defined in claim 1, 3 or 8, wherein said amount of organic material is sufficient to produce a test bias of no more than about 5%, or if said analyte is less than 100 mg/dl, no more than 5 mg/dl, whichever is greater.

* * * * *